United States Patent [19]

Monsigny et al.

[11] Patent Number: 4,703,107

[45] Date of Patent: Oct. 27, 1987

[54] WATER-SOLUBLE ACYLATED DERIVATIVES OF PEPTIDES OR AMINO ACIDS, THEIR PREPARATION AND THEIR USE

[75] Inventors: Michel Monsigny, Saint Cyr En Val; Roger Mayer, Orleans, both of France

[73] Assignee: Centre National de la Recherche Scientifique (CNRS), Paris, France

[21] Appl. No.: 804,115

[22] Filed: Dec. 3, 1985

Related U.S. Application Data

[63] Continuation-in-part of Ser. No. 610,112, May 14, 1984, abandoned.

[30] Foreign Application Priority Data

May 16, 1983 [FR] France ................... 83 08051

[51] Int. Cl.$^4$ .................... C07K 7/06; C07K 5/06; C07K 5/08; C07K 5/10
[52] U.S. Cl. .................................... 530/330; 530/331
[58] Field of Search ................. 548/227; 530/330, 331

[56] References Cited

U.S. PATENT DOCUMENTS 4,458,078  7/1984  Kitaura et al. ................... 548/227

OTHER PUBLICATIONS

Biochem. and Biophys. Res. Commun. vol. 33, (1968) 156–159.
Chem. Abstr. vol. 65, (1966) 17566.
Chem. Abstr. vol. 70, (1969) 8971h.
Chem. Abstr. vol. 102, (1985) 204299.
Chem. Abstr. vol. 100, (1984) 34817v.
Chem. Abstr. vol. 59, (1963) 5247.
Chem. Abstr. vol. 59, (1963) 1739.
Chem. Abstr. vol. 82, (1975) 43696s.
Chem. Abstr. vol. 79, (1973) 126723n.
Chem. Abstr. vol. 68, (1967) 22180.

*Primary Examiner*—Delbert R. Phillips
*Attorney, Agent, or Firm*—Cushman, Darby & Cushman

[57] ABSTRACT

Peptide derivatives of aminodrugs have longer lasting effects than the drugs without the peptide radical.

4 Claims, No Drawings

WATER-SOLUBLE ACYLATED DERIVATIVES OF PEPTIDES OR AMINO ACIDS, THEIR PREPARATION AND THEIR USE

RELATED APPLICATION

This is a continuation-in-part of Ser. No. 610,112 filed May 14, 1984 now abandoned.

The present invention relates to new water-soluble acylated derivatives of peptides or amino acids, their preparation and their use.

It is known that the colorimetric and fluorimetric dosage of proteases (or peptidases) uses various derivatives of amino acids or peptides whose N-terminal end is substituted by an acetyl, benzoyl, t-butyloxycarbonyl, benzyloxycarbonyl, glutaryl, succinyl or tosyl group and whose C-terminal end is amidified by a nitroanilide, 4-methoxy-2-naphthylamine, 7-amino-4-methyl coumarin, $\alpha$-naphthylamine, $\beta$-naphthylamine, 3-amino-9-ethylcarbazole, indolylamine or 3-amino-5-bromoindole group, or esterified by an $\alpha$- or $\beta$-naphthol or naphthol AS-D (2-methoxy anilide of 3-hydroxy-2-naphthoic acid) group. Even these derivatives can be used to make visible the proteases and peptidases in situ by enzymatic histochemical methods (Z. Lojda, R. Gossrau and T. H. Schiebler, 1979, Springer-Verlag, Berlin, pp 339). Generally, these derivatives are slightly soluble in water and it is therefore necessary to previously dissolve them in an organic solvent and then to dilute these resulting solutions in a buffer. The weak solubility of the substrates results in weak sensitivity of the protease and peptidase dosage methods and limits the possibilities of visualization by histomchemical methods.

It is also known that certain derivatives of amino acids or peptides can play the role of an enzyme inhibitor and be employed principally as medicines, for example, as suicide-substrates for the said enzymes. Here again, the preparation, the production of an appropriate galenic form and the use in vitro or in vivo of these derivatives are made difficult because of their low solubility in water.

It is further known that pro-drugs can be obtained which impart, principally, a delay effect or facilitate the transport of the drug in vivo by linking the drug (active substance) to a peptide. However, their low solubility in water often constitutes an impediment in the preparation and efficacy of these pro-drugs.

Such pro-drugs are interesting and in particular when the peptide constitutes a good substrate for a specific protease secreted by the target of the active drug (for example, by a tumoral cell or by a pathogenic microorganism). In this situation the active drug is liberated only in the environment of the target, which has for an effect to favor the efficacy of the drug.

The present invention relates to a new water-soluble acylated derivative of peptides, amino acids, or peptides or amino acids having a modified C-terminal group, wherein their N-terminal group is acylated by a polyhydroxyalkanoyl group.

The said polyhydroxyalkanoyl group possesses generally 3 to 10 carbon atoms and at least 2 hydroxyl groups. The invention extends principally to the said acylated derivatives of peptides or amino acids whose C-terminal group carries a -X substituent, such as that defined below.

Preferably, the said polyhydroxyalkanoyl group (also designated by the abbreviation, PHA) has the formula $R_1$—(CHOH)$_m$—CO—, wherein $R_1$ represents H or $CH_3$ and m is a whole number ranging from 2 to 7.

The invention has, in particular, a new acylated derivative of the formula:

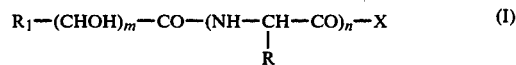

wherein $R_1$ and m are defined above, R is a lateral chain of an amino acid, n is a whole number ranging from 1 to 10 and X is an active group such as, for example, a substituent capable of imparting to the derivatives of formula I a coloration, a fluoresence or a pharmocologic activity. It will be noted however, that when n is greater than 1, the R substituents can have different values in the same compound of formula I.

Representative compounds of the present invention include, for example, those for which $R_1$—(CHOH)$_m$—CO— represents an erythronoyl, threonoyl, ribonoyl, arabinoyl, xylonoyl, lyxonoyl, gluconoyl, galactonoyl, mannonoyl, glycoheptonoyl or glycooctonoyl, residue; R represents the lateral chain of D or L amino acids, in particular, series L amino acids, selected from the following amino acids; serine, threonine, asparagine, proline, glutamine, glycine, alanine, valine, cysteine or one of its S-substituted derivatives methionine, leucine, isoleucine, phenylalanine, p-nitrophenylalanine, tyrosine or one of its O-substituted derivatives lysine, ornithine, arginine, tryptophan, aspartic acid, glutamic acid, alkyl or aryl gamma ester of aspartic acid and alkyl or aryl delta ester of glutamic acid.

In formula I, X represents, principally, a $X_1$ group which is equal to —NH—$R_2$. This —NH—$R_2$ group is derived from a $R_2$—$NH_2$ amine which can be, for example, an aromatic amine such as p-nitroaniline, $\alpha$-naphthylamine, $\beta$-naphthylamine, 4-methoxy-$\beta$-naphthylamine, 7-amino-4-methyl coumarin, 7-amino-4-trifluoromethyl-coumarin, 7-amino-4-nitro-2-oxa-1,3-benzodiazole or 3-amino-9-ethyl carbazole, or X represents an $X_2$ group which is equal to —NH—$R_3$. This —NH—$R_3$ group is derived from an amino drug $R_3$—$NH_2$ which can be, for example, an anti-tumor drug of the anthracycline group such as daunorubicin or daunomycin, puromycin, adriamycin or doxorubicin, a phenylenediamine mustard, etc... or an antimalarial drug such as primaquine or chloroquine. X can also represent another active group, $X_3$, which is capable of imparting, for example, a pharmacologic activity to the peptide of formula I. $X_3$ is, in particular, a group preserving or ameliorating the enzyme inhibiting activity, such as a —H, —OH, —CH$_2$Cl, —O—alkyl, —O—Ar (Ar being an aryl group, such as phenyl optionally substituted, for example, a nitrophenyl group),

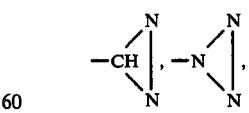

—O—Alk—Hg—Cl, or —NH—Alk—Hg—Cl (Alk being an alkylene group).

Representative derivatives of Formula I include, those which carry the sequences enumerated below. This listing, however is not limitive. These derivatives are useful as substrates, comprising there as suicide-substrates, for the following enzymes. (It is noted that the indicated sequences are the minimal sequences and that it is possible to insert 1 to 3 other amino acids between the PHA group and the indicated peptide):

chymotrypsin:
  PHA-L-Phe-X
  PHA-L-Tyr-X
PHA-L-Ala-L-Ala-L-Phe-X
  PHA-Gly-Gly-L-Pro-L-Phe-X
trypsin:
  PHA-L-Arg-X
  PHA-L-Lys-X
  PHA-L-Phe-L-Val-L-Arg-X
  PHA-L-Pro-L-Phe-L-Arg-X
  PHA-L-Phe-L-Ser-L-Arg-X
  PHA-L-Val-L-Leu-Gly-L-Arg-X
thrombin or plasmin:
  PHA-L-Phe-L-Val-L-Arg-X
  PHA-Gly-L-Pro-L-Arg-X
  PHA-Gly-L-Pro-L-Lys-X
plasmin:
  PHA-L-Ala-L-Ala-L-Lys-X
  PHA-L-Val-L-Leu-L-Lys-X
  PHA-L-Ile-L-Phe-L-Lys-X
  PHA-L-Phe-L-Ala-L-Lys-X
  PHA-L-Phe-L-Val-L-Arg-X
elastase:
  PHA-L-Ala--Ala-L-Ala-X
  PHA-L-Ala-L-Ala-L-Pro-L-Val-X
  PHA-L-Ala-L-Ala-L-Pro-L-Ala-X
  PHA-L-Ala-L-Ala-L-Pro-L-Phe-X
  PHA-L-Ala-L-Ala-L-Pro-L-Mét-X
cathepsin B:
  PHA-L-Phe-L-Val-L-Arg-X
cathepsin D:
  PHA-L-Arg-Gly-L-Phe-L-Pro-X
  PHA-L-Arg-L-Phe-L-Pro-X
  PHA-L-Ala-L-Arg-L-Arg-X
cathepsin G:
  PHA-L-Ala-L-Ala-L-Pro-L-Met-X
  PHA-L-Phe-L-Leu-L-Phe-X
papain:
  PHA-L-Arg-X
ficin or neutral peptidases:
  PHA-Gly-Gly-L-Leu-X
collagenase:
  PHA-Gly-L-Pro-L-Ala-Gly-L-Pro-X
  PHA-L-Pro-L-Ala-Gly-L-Pro-X
urokinase or plasminogen activator:
  PHA-Gly-Gly-L-Arg-X
  PHA-L-Pro-L-Phe-L-Arg-X
  PHA-L-Phe-Gly-Gly-L-Arg-X
kallikreine or plasminogen activator:
  PHA-L-Pro-L-Phe-L-Arg-X
factor $X_a$:
  PHA-L-Ile-Gly-Gly-L-Arg-X
protease of Limulus polyphemus activated by a lipopolysaccharide:
  PHA-L-Val-L-Leu-Gly-L-Arg-X
  PHA-L-Val-L-Leu-Gly-L-Lys-X In the lists of peptidic derivatives given above, each amino acid is represented by its conventional symbol. In a general fashion, in the formulae of the present application, it is assumed, by convention, that each amino acid has its N-terminal group to the left and its C-terminal group to the right.

Other substrates which may be present in the compounds of formula I are illustrated by the following compounds:

PHA-L-Ser-Gly-L-Lys-X
  PHA-L-Ile-L-Leu-L-Arg-X
  PHA-L-Ile-L-Leu-L-Lys-X
  PHA-L-Ile-L-Phe-L-Arg-X
  PHA-L-Val-L-Leu-L-Arg-X
  PHA-L-Val-L-Phe-L-Arg-X
  PHA-L-Val-L-Phe-L-Lys-X
  PHA-Gly-L-Val-L-Phe-L-Arg-X
  PHA-Gly-L-Val-L-Phe-L-Lys-X
  PHA-Gly-L-Ile-L-Phe-L-Lys-X
  PHA-Gly-L-Pro-L-Lys-X
  PHA-L-Ala-L-Ala-L-Phe-X

In the lists of substrates given above, X can have, principally, all the values designated above by $X_2$ or $X_3$ (the products are then useful as medicines) or by $X_1$ (the products are then useful principally to effect the dosages).

Among the derivatives of Formula I and without this list being limiting, are those which are enumerated below and are useful as anti-tumoral pro-drugs. They exhibit the advantage of liberating the drug only in the vicinity of the tumoral cells, under the action of the proteases secreted by them, or by other tumor-associated cells:

PHA-L-Ala-L-Ala-L-Pro-L-Ala-Daunorubicin
  PHA-L-Ala-L-Ala-L-Pro-L-Ala-L-Leu-Daunorubicin
  PHA-L-Ala-L-Ala-L-Pro-L-Ala-Adriamycin
  PHA-L-Ala-L-Ala-L-Pro-L-Ala-L-Leu-Adriamycin
  PHA-L-Ala-L-Ala-L-Pro-L-Val-Daunorubicin
  PHA-L-Ala-L-Ala-L-Pro-L-Val-L-Leu-Daunorubicin
  PHA-L-Ala-L-Ala-L-Pro-L-Val-Adriamycin
  PHA-L-Ala-L-Ala-L-Pro-L-Val-L-Leu-Adriamycin
  PHA-L-Phe-L-Val-L-Arg-Daunorubicin
  PHA-L-Phe-L-Val-L-Arg-L-Leu-Daunorubicin
  PHA-L-Phe-L-Val-L-Arg-Adriamycin
  PHA-L-Phe-L-Val-L-Arg-L-Leu-Adriamycin
  PHA-L-Phe-L-Ala-L-Lys-Danuorubicin
  PHA-L-Phe-L-Ala-L-Lys-L-Leu-Daunorubicin
  PHA-L-Phe-L-Ala-L-Lys-Adriamycin
  PHA-L-Phe-L-Ala-L-Lys-L-Leu-Adriamycin
  PHA-Gly-Gly-L-Arg-Daunorubicin
  PHA-Gly-Gly-L-Arg-L-Leu-Daunorubicin
  PHA-Gly-Gly-L-Arg-Adriamycin
  PHA-Gly-Gly-L-Arg-L-Leu-Adriamycin
  PHA-L-Pro-L-Phe-L-Arg-Daunorubicin
  PHA-L-Pro-L-Phe-L-Arg-L-Leu-Daunorubicin
  PHA-L-Pro-L-Phe-L-Arg-Adriamycin
  PHA-L-Pro-L-Phe-L-Arg-L-Leu-Adriamycin
  PHA-L-Ile-L-Phe-L-Lys-Adriamycin
  PHA-L-Ile-L-Phe-L-Lys-Daunorubicin
  PHA-Gly-L-Pro-L-Lys-Adriamycin
  PHA-Gly-L-Pro-L-Lys-Daunorubicin Representative derivatives of Formula I, useful as anti-parasitic pro-drugs, includes, without limitation, the following compounds:
  PHA-L-Val-L-Leu-Gly-L-Arg-Primaquine, and
  PHA-L-Val-L-Leu-Gly-L-Arg-Chloroquine.

Amoung the compounds of Formula I which are chromogenic substrates, the following compounds are representative:
  PHA-L-Ala-L-Ala-L-Pro-L-Ala-pNa
  PHA-L-Ala-L-Ala-L-Pro-L-Val-pNa
  PHA-L-Val-L-Leu-Gly-L-Arg-pNa
  PHA-L-Val-L-Leu-Gly-L-Lys-pNa
  PHA-L-Ser-Gly-L-Lys-pNa
  PHA-Gly-L-Pro-L-Arg-pNa PHA-Gly-L-Pro-L-Lys-pNa
PHA-L-Val-L-Leu-L-Arg-pNa
PHA-L-Val-L-Leu-L-Lys-pNa
PHA-L-Ile-L-Leu-L-Arg-pNa
PHA-L-Ile-L-Leu-L-Lys-pNa
PHA-L-Ile-L-Phe-L-Arg-pNa
PHA-L-Ile-L-Phe-L-Lys-pNa In the preceding list of compounds, pNa means "paranitroanilide"

It has now been found in accordance with the present invention, that the new derivatives of Formula I which carry a polyhydroxyalkanoyl group in the N-terminal position are soluble in very high concentrations in water or in a buffer. Thus, it is no longer necessary to previously dissolve these derivatives (substrates of proteases or peptidases) in an organic solvent. The use of these derivatives then considerably improves the sensitivity of detection methods for proteases and peptidases. It is also possible to easily determine the best peptidic substrate for a given protease, as is illustrated in Example B, below. Indeed, to increase the speed by hydrolysis, it is necessary that the concentration of free substrate is the highest possible, for example, clearly greater than the Michaelis constant. With proteases and peptidases, this contrast is in the order of magnitude of 1 mM. When the substrate is slightly soluble, it is found in the form of a dispersion of aggregates in the buffer and the effective concentration (non-aggregated substrate) is much lower than the value of the Michaelis constant. Moreover, the derivatives according to the present invention, which are very water-soluble, do not carry charges attributable to the solubilizing substituent, contrary to the derivatives whose N-terminal group is substituted by succinyl or glutaryl residues. Finally, the preparation of the derivatives of the present invention is particularly simple: the peptide or amino acid is substituted by reaction with the lactone or an active ester of the PHA of its α-amino group. Then the α-carboxylic group of the peptide or the amino acid is substituted by a suitable active group.

The invention also relates to a process for preparing the new water-soluble acylated derivatives described above, i.e. a process for preparing an acyl derivative of a peptide, of an aminoacid or of a derivative of a peptide or aminoacid having a modified C-terminal group, to obtain an acyl derivative having improved water-solubility. This process comprises principally acylating the N-terminal group of an amino acid or a peptide, or a derivative thereof having a modified C-terminal group with an acylation agent derived from a polyhydroxy alkanoic acid.

The present invention relates particularly to a process for preparing the new derivatives of Formula I. In this process there is employed as an initial reactant, an amino acid derivative or a peptide of the formula:

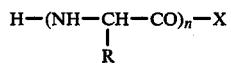

wherein
n, R and X are defined above. This initial reactant is reacted with an active derivative of a polyhydroxyalkanoic acid of the formula $$R_1-(CHOH)_m-COOH \quad \text{III}$$

wherein $R_1$ and m are defined above,
so as to obtain a compound of the formula:

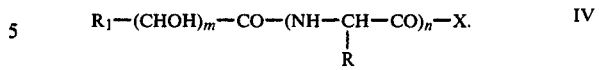

If desired the compound of formula IV can be transformed into another derivative of Formula I by employing known procedures.

In a general manner, the various transformations of a compound of Formula I into another compound of Formula I (with a different X substituent) are carried out according to known methods described in specialized works such as, for example, "Methods in Enzymology"-Proteolytic Enzymes, in particular Volumes 19, 45 and 80.

The initial peptide reactants can be purchased commercially or can be synthesized according to known peptide synthesis methods; (see for example, E. Cross and J. Meienhoffer, 1979, "The Peptides: Analysis, synthesis, biology," Academic Press, New York, Volumes I, II, III and following).

In the particular modes of execution, the process of the invention can exhibit the following characteristics taken alone or in combination:
the active derivative of the polyhydroxyalkanoic acid is a derivative capable of acylating the N-terminal group of compound II. This active derivative is, for example, the lactone corresponding to the said acid or an active ester of said acid such as, for example, the ester of N-hydroxysuccinimide;
to transform the compound of Formula IV (with X=OH) into the derivative of Formula I wherein X represents —NH—$R_2$ or —NH—$R_3$, the amine $R_2$—$NH_2$ or $R_3$—$NH_2$ is reacted in the presence of a coupling agent such as, for example, benzotriazol-1-yl-oxy-tris(dimethylamino) phosphonium hexafluorophosphate (or BOP).

The invention also relates to the use as water-soluble derivatives, of compounds selected from amino acids, peptides, amino acid with a modified C-terminal group and peptides with a modified C-terminal group, of acylated (N-terminal)derivatives of these compounds, this use being characterized by the fact that the N-terminal group of said compounds is acylated by a polyhydroxyalkanoic group.

The invention also relates principally to the use as water-soluble medicines of the acylated derivatives such as defined above possessing a pharmacologic activity and in particular derivatives of Formula I for which X=NH—$R_3$, $R_3$ representing the residue of an amino drug or, indeed, X can represent a $X_3$ group selected from —H, —OH, —$CH_2Cl$, —O—alkyl, —O—Ar (Ar being an aryl group such as phenyl, optionally substituted, for example a nitrophenyl group),

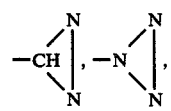

—O—Alk—Hg—Cl, or —NH—Alk—Hg—Cl
(Alk being an alkylene group).

However, the invention extends to pharmaceutical compositions containing at least one compound of Formula I as an active component, optionally in combination with an appropriate excipient.

When the derivatives of Formula I are pro-drugs they are used with doses corresponding to conventional doses of the active drug with the same therapeutic indications as the said active drug.

Generally, the toxicity of the pro-drugs is lower than that of the corresponding drug.

When the medicines of the invention are enzyme inhibitors they are used, principally as preventive treatment agents for the formation of metastases and the proliferation of tumors. The effective doses vary generally from 0.1 to 10 mg/kg.

The medicines of the invention are administered by any suitable method. It is necessary to note however that an oral method is generally not convenient.

These medicines can be provided principally in the form of injectable solutions, lyophilized powders to be diluted in a physiologic serum, solutions or emulsions for application to the skin or mucous membranes and solutions packaged in pressurized containers as aerosols.

The following non-limiting examples illustrate the present invention.

EXAMPLE 1

Elastase substrate

The peptide, L-Ala-L-Ala-L-Pro-L-Ala (1 mmole), synthesized by known methods of peptidic synthesis, is dissolved in dimethylsulfoxide (5 ml) in the presence of N-trimethylbenzylamine (in the form of N-trimethylbenzylammonium methoxide—2 mmoles). To this solution, gluconodelta-lactone (2 mmoles) is added. The solution is stirred at 50° C. for 15 hours.

The PHA-peptide (gluconoyl peptide) is purified by chromatography on a silica column (3×30 cm) in the solvent system ($CHCl_3/CH_3OH/H_2O/CH_3CO_2H$, 8:6:1:1 by volume). The solution containing the PHA-peptide is evaporated to dryness. The residue (oil) is taken up in N-dimethylformamide (3 ml) at 4° C.

To a solution of the PHA-peptide (1 mmole) in dry N-dimethylformamide and deprived of amine (2 ml), 1-hydroxybenzotriazole (1 mmole), dicyclohexylcarbodiimide (1 mmole) and A.E.C. (3-amino-9-ethyl-carbazole—1 mmole) are added. The solution is stirred at 4° C. for 2 hours, then at 25° C. for 18 hours. The solution is then cooled at 4° C. for 1 hour to favor the precipitation of the dicyclohexyl-urea which is then removed by filtration. The N-dimethylformamide is evaporated under reduced pressure at 50° C. The PHA-L-Ala-L-Ala-L-Pro-L-Ala-AEC is purified by chromatography on a silica gel column (3×30 cm), equilibrated in the solvent system, $CHCl_3/CH_3OH/CH_3CO_2H$, 80:30:5, by volume. The PHA-L-Ala-L-Ala-L-Pro-L-Ala-AEC is detected by its absorbence at 340 nm. Its purity is confirmed by thin layer chromatography. The fractions containing the comound are concentrated to dryness. The residue is taken up in 2 ml of water and the solution is lyophilized (Yield: 80%).

The PHA-L-Ala-L-Ala-L-Pro-L-Ala-AEC is also characterized by infra-red spectrometry—characteristic bands in $cm^{-1}$: hydroxyl=3320, amide I—1640, amide II—1535, aromatic groups—1490; by ultraviolet spectrophotometry: maximum absorption at 340 nm, minimum at 315 nm; by spectrofluorimetry: maximum excitation wave length 342 nm, minimum emission wave length—390 nm, and by protonmagnetic resonance.

The solubility of the PHA-L-Ala-L-Ala-L-Pro-L-Ala-AEC is greater than 80 mg/ml in distilled water or a buffer with a pH between 3 and 9.

EXAMPLE 2

Elastase substrate

The peptide, L-Ala-L-Ala-L-Pro-L-Val-OBzl is synthesized by known methods for peptidic synthesis. The symbol Bzl is the known symbol designating the benzylic ester derivative. The benzylic ester group was selected to protect the C-terminal end of the peptide during the peptidic synthesis, and to permit a simple detection of the peptides and their derivatives in the course of the purification steps by chromatography.

The peptide, L-Ala-L-Ala-L-Pro-L-Val-OBzl. HCl (2 mmoles) is dissolved in dimethyl sulfoxide (3 ml). To this solution, triethylamine (6 mmoles) and glucono-deltalactone (6 mmoles) are added. The solution is stirred at 50° C. for 15 hours.

The PHA-peptide-OBzl (PHA=gluconoyl) is purified on a silica column (3×30 cm) equilibrated with the solvent system, $CHCl_3/CH_3OH/CH_3CO_2H$ : 50:20:1 by volume. The fractions containing the PHA-peptide are collected and the solvent is evaporated under reduced pressure.

The residue (oil) is taken up in methanol (6 ml) containing 10% water and hydrogenolyzed for 4 hours in the presence of 200 mg of palladium on carbon (10% Pd). The reaction mixture is filtered and evaporated to dryness.

The PHA-peptide-OH (1 mmole) is dissolved in N-dimethylformamide (2 ml). To this solution, 1-hydroxy benzotriazole (1 mmole), dicyclohexylcarbodiimide (1 mmole) and 3-amino-9-ethyl carbazole (1 mmole) are added. The solution is stirred initially for 2 hours at 4° C., then for 18 hours at 25° C. under an inert atmosphere. Then, the solution is cooled to favor the complete precipitation of dicyclohexylurea which is removed by filtration. The N-dimethylformamide is evaporated under a vacuum and the PHA-peptide-AEC is purified by chromatography on a silica gel column (3×30 cm) equilibrated with the solvent system, $CHCl_3/CH_3OH/CH_3CO_2H$, 80:30:5 by volume (Yield: 80%).

The PHA-L-Ala-L-Ala-L-Pro-L-Val-AEC has the characteristics corresponding to the PHA group, to the peptidic linkages and to the AEC group as indicated in Example 1.

EXAMPLE 3

Chymotrypsin substrate

The hydrochloride of the methyl ester of L-phenylalanine, L-Phe-OCH3HCl, (2 mmoles) is dissolved in dimethylsulfoxide (3 ml). To this solution, glucono-delta-lactone (6 mmoles) and N-triethylamine (6 mmoles) are added. The solution is stirred at 50° C. for 15 hours. The PHA-L-Phe-OCH3 (PHA=gluconoyl) is purified by chromatography on a silica gel column (3×30 cm) equilibrated in the solvent system, $CHCl_3/CH_3OH/H_2O/CH_3CO_2H$, 8:6:1:1 by volume. The PHA-L-Phe-OCH3 is then saponified in a solution of methanol/water (1:1, v/v) adjusted to a pH of 10.5 by the addition of 2N NaOH for 12 hours. The PHA-L-Phe-OH is purified on a silica gel column (3×30 cm) equilibrated in the solvent system, $CHCl_3/CH_3OH/CH_3CO_2H/H_2O$, 6:6:1:1 by volume.

The PHA-L-Phe-OH (1 mmole) is substituted by AEC under the conditions described in Example 1.

The PHA-L-Phe-AEC exhibits characteristics corresponding to the PHA group, to the aromatic rings AEC and Phe, as well as to the amide linkages, as indicated in Example 1.

EXAMPLE 4

Collagenase substrate

In a manner analogous to that described in Example 1, the peptide, L-Pro-L-Ala-Gly-L-Pro-OBzl. HCl (synthesized in accordance with known methods of peptidic synthesis is converted into the PHA-L-Pro-L-Ala-Gly-L-Pro-AEC derivative (PHA=gluconoyl) Yield : 60%.

The PHA-L-Pro-L-Ala-Gly-L-Pro-AEC exhibits the characteristics corresponding to the PHA group, to the peptidic linkages and to the AEC group, as indicated in Example 1.

EXAMPLE 5

Another collagenase substrate

In a manner analogous to that described in Example 1, the derivative, Gly-L-Pro-L-Ala-Gly-L-Pro-OBzl.HCl (synthesized by known methods of peptidic synthesis) is converted into the derivative PHA-Gly-L-Pro-L-Ala-Gly-L-Pro-AEC (PHA=gluconoyl) Yield : 60%.

The PHA-Gly-L-Pro-L-Ala-Gly-L-Pro-AEC exhibits the characteristics corresponding to the PHA group, to the peptidic linkages and to the AEC group, as indicated in Example 1.

EXAMPLE 6

Prodrug

The PHA-L-Ala-L-Ala-L-Pro-L-Val prepared as described in Example 2 is coupled to daunorubicin under the same conditions as for AEC.

The gluconoyl derivative, PHA-L-Ala-L-Ala-L-Pro-L-Val-daunorubicine, exhibits the characteristics corresponding to the PHA group, to he peptidic linkages and to the aglycone of daunorubicine determined by infra red spectroscopy, absorptiometry fluorimetry and nuclear magnetic resonance.

In an analogous manner, the gluconoyl derivative, PHA-L-Ala-L-Ala-L-Pro-L-Val-L-Leu-Daunorubicin, useful as a pro-drug, is also produced.

EXAMPLE 7

Prodrugs

Analogously, the gluconoyl derivatives PHA-L-Ala-L-Ala-L-Pro-L-Val-adriamycine and PHA-L-Ala-L-Ala-L-Pro-L-Val-L-Leu-adriamycine are prepared as the derivative of daunorubicin in Example 6.

EXAMPLE 8

In a similar manner the following gluconoyl derivatives are prepared
PHA-L-Phe-L-Pro-L-Arg-Adriamycin,
PHA-L-Phe-L-Pro-L-Arg-Daunorubicin,
PHA-L-Phe-L-Pro-L-Arg-L-Leu-Adriamycin, and
PHA-L-Phe-L-Pro-L-Arg-L-Leu-Daunorubicin,
PHA-Gly-L-Pro-L-Lys-Adriamycin,
PHA-L-Ile-L-Leu-L-Lys-Adriamycin,
PHA-L-Val-L-Leu-L-Lys-Adriamycin,
the compounds being useful as prodrugs.

EXAMPLE 9

In an analogous manner the following gluconoyl compound is prepared:
PHA-L-Val-L-Leu-Gly-L-Arg-Primaquine, which is useful as an antimalaria prodrug.

EXAMPLE 10

In this example:
Boc means t-butoxycarbonyl
OBzl means benzyl ester
Lys (Z) means lysine with epsilon-$NH_2$ protected by benzyloxy carbonyl
TEA means triethylamine
DDCI means dicyclohexylcarbodiimide
GlcA means gluconoyl
HOBt means 1-hydroxybenzotriazole
ACOH means acetic acid
DCHA means: dicyclohexylamine
DCHU means: dicyclohexylurea
BOP means: benzotriazolyloxytri (dimethylamino) phosphonium hexafluorophosphate.

A—Synthesis of GlcA-Ile-Phe-Lys-AEC
N-Boc-Ile-Phe-OBzl

A solution of HCl, H-Phe-OBzl (2,0 g, 6,88 mmol) and of Boc-Ile-OH, DCHA, (2.8 g, 6.88 mmol) in chloroform (50 ml) was cooled at $-10°$ C. and dicyclohexylcarbodimide (1.56 g, 7.57 mmol) was added. The reaction mixture was stirred for 2 h at $-10°$ C. and stored overnight at room temperature. The DCHU and HCl, DCHA formed were removed by filtration and the filtrate was washed successively with 5% Na $HCO_3$, water, 10% citric acid and water. The organic phase was dried over $Na_2SO_4$, concentrated and precipitated in hexane to give 2.99 g of a white solid, yield 93%; mg 110°–112°; $[\alpha]_{546}^{25} = -19.9°$ (c=1, McOH); $R_{f(D)}=0.82$.

HCl, H-Ile-Phe-OBzl

A solution of Boc-Ile-Phe-OBzl (2.1 g, 4.5 mmol) in 1N HCl/AcOH (23 ml) was stirred for 20 min. The excess of reagent was removed by evaporation under reduced pressure and the residue was triturated several time with hexane. The precipitate was dried to yield 1.75 g (96%); m.p. 168°–170° C.; $[\alpha]_{546}^{25} = +19.6$ (c=1, MeOH) $R_{f(D)}=0.60$; argentimetric titration 99%.

GlcA-Ile-Phe-OBzl

To a solution of HCl, H-Ile-Phe-OBzl (1.41 g, 3.5 mmol) in freshly distilled DMF (2 ml) neutralized with triethylamine (0.49 ml, 3.5 mmol), δ-gluconolactone (1.25 g, 7 mmol) and TEA (0.98 ml, 7 mmol) were added. The mixture was stirred at 60° C. for 24 hr. δ-gluconolactane (0.63 g, 3.5 mmol) and TEA (0.43 ml, 3.5 mmol) were then added and the mixture was stirred for 24 h more. The mixture was then filtered and the filtrate evaporated under reduced pressure. The residue was purified by preparative chromatography on a silica gel column eluted with the system chloroform-methanol-water (16:6:1): yield 1.1 g (58%) after precipitation in ether-petroleum ether (1:1, v/v); mp 175°–176° C.; $[\alpha]_{546}^{25} = +1.3°$ (c=1, DMF); $R_{f(A)}=0.53$.

GlcA-Ile-Phe-OH

GlcA-Ile-Phe-OBzl (1.04 g, 1.9 mmol) was hydrogenolyzed in presence of palladium/activated charcoal (10% Pd) (200 mg) in DMF-water (9:1, v/v) solution for 5 h. After removal of the catalyst by filtration the solution was evaporated to dryness and the product was recovered by lyophilization from water with 98% yield (0.85 g); mp 173°–174° C.; $[\alpha]_{546}^{25} = +3.36$ (c=1, MeOH); $R_{f(A)}=0.15$.

Boc-Lys(Z)-AEC

The title compound was synthesized by coupling Boc-Lys(Z)-OH,DCHA (2.7 g, 4.8 mmol) and 3-amino-9-ethylcarbazole (1 g, 4.8 mmol) in the presence of BOP (2,12 g, 4,8 mmol) in freshly distilled DMF (5 ml). The mixture was stirred in the dark and under nitrogen atmosphere, at room temperature for 6 h. The HCl, DCHA salt formed was removed by filtration and the filtrate was evaporated to dryness. The residue was dissolved in ethyl acetate and washed succesively with 5% NaHCO₃, water, 10% citric acid and water. The organic phase was dried over Na₂SO₄ and concentrated. The residue was precipitated in ether-petroleum ether (1:1, v/v). The precipitate was filtered and dried to give 2,2 g: yield 80%; mp 114° C. $[\alpha]_{546}^{25} = +23.0°$ (c=1, MeOH); $R_{f(c)}=0.80$.

HCl,H-Lys(Z)-AEC

A solution of Boc-Lys(Z)-AEC (2.0 g, 3.5 mmol) in 1N HCl/AcOH (18 ml) was stirred for 20 min. at room temperature. The excess of reagent was removed by evaporation under reduced pressure and the residue was dissolved in chloroform and precipitated in dry ether. The precipitate was filtered and dried to give 1.74 g (98% yield); mp 117°–119° C.; $[\alpha]_{546}^{25} = +62.9$ (c=1, MeOH); $R_{f(c)}=0.09$; argentimetric titration 99%.

Glc A-Ile-Phe-Lys(Z)-AEC

The title compound was obtained by coupling the two fragments Glc A-Ile-Phe-OH (0.82 g, 1.8 mmol) and HCl, H-Lys(Z)-AEC (0.9 1.8 mmol) in distilled DMF (4 ml) in presence of TEA (0,25 ml, 1,8 HOBT.-H₂O (0.27 g, 1.8 mmol) and DCCI (0.41 g, 2 mmol). The reaction mixture was stirred 2 h at −10° C. and overnight at room temperature. The DCHU and HCl, TEA formed were removed by filtration and the filtrate was evaporated to dryness. The crude product was recrystallized from isopropanol to give 1.4 g (86% yield); mp 201°–203° C.; $R_{f(B)}=0.56$.

Glc A-Ile-Phe-Lys-AEC, HCl

Glc-Ile-Phe-Lys(Z)-AEC (1 g, 1.1 mmol) was dissolved in DMF-water (9:1, v/v) (4 ml) and hydrogenolyzed over Pd/C (10%) (200 mg) in presence of 1 n HCl (1,3 ml) for 2 h. After removal of the catalyst by filtration, the filtrate was evaporated to dryness. The residue was taken up with methanol and precipitated in ether-petroleum ether (1:1, v/v) yield 0.83 g (93%); mp 170°–171° C.; $R_{f(c)}=0.10$;

A summary of the solubilities in 50 mM Tris-HCl (pH 8,1) buffer of some illustrative substrates which were synthesized is given in Table I. In order to study the influence of the hydrophilic properties of the gluconoyl group on the substrate affinity for plasmin, some substrates with hydrophobic N-acylating group such as benzyloxycarbonyl (Z) or tertiobutyloxycarbonyl (Boc), were also synthesized.

All the substrates synthetized are water stable, showing no detectable spontaneous hydrolysis after a 5 h, incubation under assay conditions.

B. In an analogous manner, further derivatives were prepared and are listed in Table I.

TABLE I

| Substrates (chlorhydrate) | Solubility mM at 20° C. |
|---|---|
| GlcA—Ile—Leu—Lys—AEC | 94 |
| GlcA—Ile—Phe—Lys—AEC | 0.54 |
| GlcA—Val—Leu—Lys—AEC | 250 |
| GlcA—Val—Phe—Lys—AEC | 165 |
| GlcA—Gly—Val—Phe—Lys—AEC | 4.2 |
| GlcA—Gly—Ile—Phe—Lys—AEC | 2.5 |
| GlcA—Gly—Pro—Lys—AEC | 380 |
| GlcA—Ile—Leu—Arg—AEC | 143 |
| GlcA—Ile—Phe—Arg—AEC | 1.1 |
| GlcA—Val—Leu—Arg—AEC | 227 |
| GlcA—Val—Phe—Arg—AEC | 100 |
| GlcA—Gly—Val—Phe—Arg—AEC | 3.6 |
| GlcA—Val—Leu—Gly—Arg—AEC | 67 |
| GlcA—Val—Leu—Gly—Lys—AEC | 62 |
| GlcA—Ser—Gly—Lys—AEC | 54 |
| Boc—Ile—Phe—Lys—AEC | 0.04 |
| Z—Ile—Phe—Lys—AEC | 0.03 |
| Boc—Val—Leu—Lys—AEC | 2.5 |
| Z—Gly—Pro—Lys—AEC | 0.2 |

It can be seen from Table I that even strongly hydrophobic sequences such as Ile-Leu-Lys, Ile-Phe-Lys and Val-Phe-Lys may have improved solubilities when they are in the form of polyhydroxyalkanoyl derivatives.

EXAMPLE 11

The following chromogenic substrates were synthetized by coupling the GlcA-di- or GlcA-tri-peptides and the paranitronilides of Arg, Ala, Val or Lys (Fmoc). Lys(Fmoc) means fluorenyl-methoxy-carbonyl derivative of lysine, a commercial product. The F-moc moiety is easily removed in weakly basic medium.
Chromogenic substrates:
 Glc A-L-Ala-L-Ala-L-Pro-L-Ala-pNa
 Glc A-L-Ala-L-Ala-L-Pro-L-Val-pNa
 Glc A-L-Val-L-Leu-Gly-L-Arg-pNa
 Glc A-L-Val-L-Leu-Gly-L-Lys-pNa
 Glc A-L-Ser-Gly-L-Lys-pNa
 Glc A-Gly-L-Pro-L-Arg-pNa
 Glc A-Gly-L-Pro-L-Lys-pNa
 Glc A-L-Val-L-Leu-L-Arg-pNa
 Glc A-Val-L-Leu-L-Lys-pNa
 Glc A-L-Ile-L-Leu-L-Arg-pNa
 Glc A-L-Ile-L-Leu-L-Lys-pNa
 Glc A-L-Ile-L-Phe-L-Arg-pNa
 Glc A-L-Ile-L-Phe-L-Lys-pNa

EXAMPLE 12

Synthesis of the prodrug
 Glc A-L-Ile-L-Phe-L-Lys-Adriamycin
H-Lys (Fmoc)-OH was converted into the corresponding NPS-Lys (Fmoc)-OH derivative, and then into NPS-Lys (Fmoc)-Adriamycin. After removal of the NPS group, the resulting hydrochloride HCl.H-Lys (Fmoc)-Adriamycin was reacted with the gluconoyl dipeptide GlcA-Ile-Phe-OH prepared as in Example 10. After removal of the F-moc groups in weakly basic medium, the title compound was obtaind.
NPS means: ortho-nitrophenyl sulfenyl.

EXAMPLE 13

Chymotrypsin substrate: Ribonoyl derivative

The peptide, H-L-Ala-L-Ala-L-Phe-7-amido-4 methyl coumarin, TFA (1m mole), synthesized by known methods of peptidic synthesis, is dissolved in 3 ml dimethylformamide containing 10% water. To this solution, triethylamine (3m moles) and ribono-lactone (3m moles) are added. The solution is stirred at 50° C. for 48 hours.

The solvent is evaporated under vacuum and the ribonoylpeptide-AMC is purified by chromatography on a silica gel column (3×30 cm) equilibrated with the solvent system $CHCl_3/MeOH/H_2O$ (80:40:5 by volume). The fractions containing the compound are concentrated to dryness. The residue is taken up in water and the solution is lyophilized (Yield: 75%).

The ribonoyl-L-Ala-L-Ala-L-Phe-AMC substrate exhibits physicochemical characteristics corresponding to the PHA group, to the acyl-AMC fluorescent group and to the amide linkage as indicated in Example 1. The solubility of this compound in distilled water is 2.0 mM/l at 20° C.

AMC means 7-amido-4-methyl coumarin.

EXAMPLE 14

Chymotrypsin substrate: Gluconoyl derivative

By analogy to example 14, the peptide H-L-Ala-L-Ala-L-Phe-AMC, TFA (1m mole) synthesized in accordance with known methods of peptidic synthesis, is converted in 70% yield into gluconoyl-L-Ala-L-Ala-L-Phe-AMC using 3 equivalents of delta-gluconolactone. The same chromatographic system was used.

The solubility of this chymotrypsin substrate in distilled water is 2.4 mM/L at 20° C.

EXAMPLE 15

Chymotrypisin substrate: Glucooctanoyl derivative

By analogy to example 14 the peptide H-L-Ala-L-Ala-L-Phe-AMC, TFA (1m mole) is converted in 55% yield into glucooctanoyl-L-Ala-L-Ala-L-Phe-AMC using 3 equivalents of glucooctanoic acid lactone. The same chromatographic system was used.

The solubility of this chymotrypsin substrate in distilled water is 3.2 mM/l at 20° C.

Examples of use

A. Elastase dosage (a) Kinetic dosage

The gluconoyl peptide, PHA-L-Ala-L-Ala-L-Pro-L-Ala-AEC is dissolved in a 0.05M Tris-HCl buffer, pH 8.8, so as to obtain an optical density at 340 nm of 0.1 for 1 cm of optical path ($4.3\times10^{-5}M$). The solution thus obtained is adjusted to 37° C. and 10 microliters of an elastase solution (1.0 to 100 micrograms/ml) are added to 1 ml of the peptide solution in fluorimetry dish. The dish is immediately introduced into the spectrofluorimeter whose sample compartment is thermostated at 37° C. The length of the excitation wave is 352 nm, the length of the emission wave is 460 nm. The "emission" signal is recorded for 3 min. The activity of the enzyme is determined by the slope of the curve obtained. The values of the slope corresponding to 10 ng, 50 ng, 100 ng, 200 ng, 500 ng and 1 microgram of elastase are reported on a graph. Under these conditions, the intensity of fluorescence measured is proportional to the amount of enzyme added to the reaction medium.

(b) Classical dosage

The peptide, PHA-L-Ala-L-Ala-L-Pro-L-Ala-AEC is dissolved in a 0.05M tris-HCl buffer, pH 8.8, in order to obtain an optical density at 340 nm of 0.1 for an optical path of 1 cm. This solution is divided into silicon hemolysis tubes (1 ml per tube). In each tube there are added 10 microliters of an elastase solution in a Tris-HCl buffer, pH 8.8, containing 0/0.5/1/2/5/10 ng of elastase. The tubes are maintained at 37° C. for 30 minutes. The reaction is stopped by the addition of 0.3 ml of N-diemthylformamide containing benzamidinium chloride (40 mM). The intensity of fluorescence is measured at 460 nm; the excitation wave length is 352 nm. The intensities obtained corrected by the intensity of the blank are placed on a graph as a function of the elastase concentration. Under these conditions, the corrected fluorescence intensity is proportional to the elastase concentration. Thus it is possible to evidence concentration as weak as one nanogram of elastase per ml, or a 40 picomolar concentration or even $1.2\times10^{-7}$ U/ml.

(c) Michaelis constant

The Michaelis constant corresponding to the peptide, PHA-L-Ala-L-Ala-L-Pro-L-Ala-AEC is determined by measuring the activity of elastase (10 ng/ml) placed in the presence of the peptide at concentrations between $4.2\times10^{-4}M$ and $4.3\times10^{-5}M$. The intensities of fluorescence obtained after 30 minutes at 37° C. are used to draw a Lineweaver-Burck diagram. The straight line obtained permits the determination of the Michaelis constant which is equal to 0.3 mM.

B. Dosage of a protease of Plasmodium falciparum

The principle of this dosage is given below:

Erythrocytes infested by parasites are lysed with a surface active agent. To the resulting lysate the PHA-peptidyl-AEC gluconoyl derivative was added and the resulting solution is incubated at 37° C. for 45 minutes. Then the AEC liberated by a protease of the parasite is extracted by ethylacetate, and the dosage of the AEC liberated is carried out by spectrofluorimetry (M. Monsigny et al. The EMBO J., 1, 303–306, 1982).

By using this method with various peptides, it has been found that the peptide present in the derivative, PHA-L-Val-L-Leu-Gly-L-Arg-AEC was the peptidic substrate most easily hydrolyzed by the proteases of the parasite.

In these tests, the surface active agent was gluconoylaminododecane.

C. Properties of prodrugs

As an example, the gluconoylderivative PHA-L-Ala-L-Ala-L-Pro-L-Val-L-Leu-Adriamycin is soluble in water. It is hydrolyzed by leucocytic elastase or the proteases of tumoral origin by liberating the active drug: L-Leu-Adriamycin. The prodrug does not penetrate normal cells (lymphocytes) or tumors (leucemic cells L1210, or Lewis lung carcinoma "3LL". To the contrary, the active drug L-Leu-Adriamycine liberated by the action of the proteases, penetrates the tumor cells and causes the death of these cells.

The gluconoylderivative PHA-L-Phe-L-Pro-L-Arg-L-Leu-Adriamycin is soluble in water. It is hydrolyzed by trypsin and by plasmin liberating the active drug L-Leu-Adriamycin. This prodrug behaves vis-a-vis tumoral cells as the prodrug described above.

D. Toxicity of prodrugs

The toxicity of the prodrugs
GlcA-Gly-Pro-Lys-Adriamycin and GlcA-Ile-Phe-Lys-Adriamycin was studied on mice after two intravenous injections at days 0 and 2. The results are summarized in Table II below.

TABLE II

| Drugs | Doses mg/kg/ injection | Number of surviving mice at day 8 | Weight variation at day 8 | Number of surviving mice at day 30 |
|---|---|---|---|---|
| ADR | 19,7 | 0/8 | −17,8% | 0/8* |
| GlcA—Gly—Pro—Lys—ADR | 35,1 | 8/8 | +15,2% | 8/8** |
| GlcA—Ile—Phe—Lys—ADR | 37,0 | 8/8 | +14,7% | 8/8** |
| Physiological saline | — | 8/8 | +18,5% | 8/8** |

*Apparent lesions: ++
**No apparent lesion.

E-Influence of the length of the polyhydroxyalkanoyl group on the water solubility of a chymotrypsin substrate The influence of the length of the N-acylating polyhydroxyalcanoyl group on the water solubility of fluorogenic substrates is shown in Table III in the case of a chymotrypsin specific substrate PHA-L-Ala-L-Ala-L-Phe-7-amido-4-methylcoumarin.

The gluconoyl has been preferred due to the low cost of the starting δ-gluconolactone. Depending on the peptidic sequence this N-acylating group, bearing five hydroxyls, leads to derivatives which are 10 to 100 times more soluble in aqueous solution than the same substrates acylated by classical groups such as N-acetyl-, N-benzyloxycarbonyl-, N-t-butyloxycarbonyl-, etc . . .

TABLE III—Influence of the length of the polyhydroxyalkanoyl group on the water solubility of the chymotrypsin substrate PHA-L-Ala-L-Ala-L-Phe-7-amido-4-methyl-coumarin. Comparison between acetyl, ribonoyl, gluconoyl and glucooctonoyl derivatives.

| SUBSTRATES | SOLUBILITY (mM AT 20° C.) |
|---|---|
| *Ac—Ala—Ala—Phe—AMC | 0.20 |
|  | 2.0 |
|  | 2.4 |
|  | 3.2 |

*Ac means acetyl

F-Plasmin Assay

The PHA-peptidyl-AEC substrates were dissolved in a 50 mM Tris-HCl buffer, absence of DMSO, at pH 8.1 which was the optimal pH for plasmin activity. The kinetic constants were calculated according the lineweaver Burk method based on initial rate determinations at eight different substrate concentrations ranged between 20 μM and 500 μM in the presence of 3 to 10 μg plasmin/ml, depending on the substrate. The amount of AEC released was a linear function of time. Slopes and intercepts were calculated by the least squares method. After incubation for 30 min. at 37° C., the free AEC was quantitatively extracted by 1 vol. ethylacetate and assessed spectrofluorometrically as described in FEBS Letters (1983), 157, 265-270. In ethylacetate, assays were conducted at excitation and emission wavelengths of 370 and 430 nm respectively. The catalytic constant k cat was calculated by dividing the velocity of the reaction by the molar concentration of the enzyme. The molecular weight of plasmin was taken as 75,400 in the calculations The results are also summarized in Table IV:

TABLE IV

| SUBSTRATES | $K_m$ (mM) | $K_{cat}$ (s$^{-1}$) | $K_{cat}/K_m$ (M$^{-1}$s$^{-1}$) | Solubility (mM) | Solubility $K_m$ |
|---|---|---|---|---|---|
| GlcA—Ile—Leu—Lys—AEC | 0.21 | 0.119 | 570 | 94 | 448 |
| GlcA—Val—Leu—Lys—AEC | 1.00 | 0.096 | 96 | 250 | 250 |
| GlcA—Val—Phe—Lys—AEC | 1.43 | 0.204 | 143 | 165 | 115 |
| GlcA—Gly—Val—Phe—Lys—AEC | 0.71 | 0.348 | 490 | 4.2 | 5.9 |
| GlcA—Gly—Pro—Lys—AEC | 0.20 | 0.020 | 100 | 380 | 1900 |
| GlcA—Ile—Leu—Arg—AEC | 1.00 | 0.032 | 32 | 143 | 143 |
| GlcA—Val—Leu—Arg—AEC | 1.33 | 0.103 | 77 | 227 | 170 |
| GlcA—Val—Phe—Arg—AEC | 1.17 | 0.206 | 175 | 100 | 85 |
| GlcA—Gly—Val—Phe—Arg—AEC | 0.50 | 0.166 | 332 | 3.6 | 7.2 |
| GlcA—Val—Leu—Gly—Arg—AEC | 0.70 | 0.126 | 180 | 67 | 96 |

Kinetic constants of the hydrosoluble substrates of plasmin measured in 50 ml Tris-HCl buffer, pH 8.1, at 37° C. GlcA means: gluconoyl

What is claimed is:

1. A water-soluble acyl derivative of a peptide having a —CO—X terminal group wherein —X represents a —NH—R$_3$ group derived from an aminodrug selected from the group consisting of antibiotics, antitumoral and antiparisitic drugs, said peptide being selected form the group consisting of -L-Phe-, L-Tyr-, -L-Ala-L-Ala-L-Phe-, -Gly-Gly-L-Pro-L-Phe-, -L-Arg-, -L-Lys-, -L-Phe-L-Val-L-Arg-, -L-Pro-L-Phe-L-Arg-, -L-Phe-L-Ser-L-Arg, -L-Val-L-Leu-Gly-L-Arg-, -Gly-L-Pro-L-Arg-, -Gly-L-Pro-L-Lys-, -L-Ala-L-Ala-L-Lys-, -L-Val-L-Leu-L-Lys-, -L-Ile-L-Phe-L-Lys-, -L-Phe-L-Ala-L-Lys-, -L-Ala-Ala-L-Ala-, -L-Ala-L-Ala-L-Pro-L-Val, -L-Ala-L-Ala-L-Pro-L-Ala-, -L-Ala-L-Ala-L-Pro-L-Phe-, -L-Ala-L-Ala-L-Pro-L-Met-, -L-Arg-Gly-L-Phe-L-Pro-, -L-Arg-L-Phe-L-Pro, -L-Ala-L-Arg-L-

Arg-, -L-Phe-L-Leu-L-Phe-, -Gly-Gly-L-Leu-, -Gly-L-Pro-L-Ala-Gly-L-Pro-, -L-Pro-L-Ala-Gly-L-Pro-, -Gly-Gly-L-Arg-, -L-Phe-Gly-Gly-L-Arg-, -L-Ile-Gly-Gly-L-Arg-, -L-Val-L-Leu-Gly-L-Lys-, -L-Ser-Gly-L-Lys-, -L-Ile-L-Leu-L-Arg-, -L-Ile-L-Leu-L-Lys-, -L-Ile-L-Phe-L-Arg-, -L-Val-L-Leu-L-Arg-, -L-Val-L-Phe-L-Arg-, -L-Val-L-Phe-L-Lys-, -Gly-L-Val-L-Phe-L-Arg-, -Gly-L-Val-L-Phe-L-Lys- and -Gly-L-Ile-L-Phe-L-Lys, the N-terminal group of said peptide being acylated by a polyhydroxyalkanol selected from the group consisting of erythrononyl, threonoyl, ribononyl, arabinonyl, xylonoyl, lyxonoyl, gluconoyl, galactonoyl, mannonoyl, glycoheptonoyl and glycooctonoyl.

2. A water-soluble acyl derivative of a peptide having a —CO—X terminal group wherein —X represents a —NH—R$_3$ group derived from an aminodrug selected form the group consisting of daunorubicin, adriamycin, primaquine and chloroquine, said peptide being selected form the group consisting of -L-Phe-, L-Tyr-, -L-Ala-L-Ala-L-Phe-, -Gly-Gly-L-Pro-L-Phe-, -L-Arg-, -L-Lys-, -L-Phe-L-Val-L-Arg-, -L-Pro-L-Phe-L-Arg-, -L-Phe-L-Ser-L-Arg, -L-Val-L-Leu-Gly-L-Arg-, -Gly-L-Pro-L-Arg-, -Gly-L-Pro-L-Lys-, -L-Ala-L-Ala-L-Lys-, -L-Val-L-Leu-L-Lys-, -L-Ile-L-Phe-L-Lys-, -L-Phe-L-Ala-L-Lys-, -L-Ala-Ala-L-Ala-, -L-Ala-L-Ala-L-Pro-L-Val, -L-Ala-L-Ala-L-Pro-L-Ala-, -L-Ala-L-Ala-L-Pro-L-Phe-, -L-Ala-L-Ala-L-Pro-L-Met-, -L-Arg-Gly-L-Phe-L-Pro-, -L-Arg-L-Phe-L-Pro, -L-Ala-L-Arg-L-Arg-, -L-Phe-L-Leu-L-Phe-, -Gly-Gly-L-Leu-, -Gly-L-Pro-L-Ala-Gly-L-Pro-, -L-Pro-L-Ala-Gly-L-Pro-, -Gly-Gly-L-Arg-, -L-Phe-Gly-Gly-L-Arg-, -L-Ile-Gly-Gly-L-Arg-, -L-Val-L-Leu-Gly-L-Lys-, -L-Ser-Gly-L-Lys-, -L-Ile-L-Leu-L-Arg-, -L-Ile-L-Leu-L-Lys-, -L-Ile-L-Phe-L-Arg-, -L-Val-L-Leu-L-Arg-, -L-Val-L-Phe-L-Arg-, -L-Val-L-Phe-L-Lys-, -Gly-L-Val-L-Phe-L-Arg-, -Gly-L-Val-L-Phe-L-Lys- and -Gly-L-Ile-L-Phe-L-Lys, the N-terminal group of said peptide being acylated by a polyhydroxyalkanol selected from the group consisting of erythrononyl, threonoyl, ribononyl, arabinonyl, xylonoyl, lyxonoyl, gluconoyl, galactonoyl, mannonoyl, glycoheptonoyl and glycooctonoyl.

3. A water-soluble acylated derivative selected from the group consisting of (1) PHA-L-Ala-L-Ala-L-Pro-L-Ala-Daunorubicin,
(2) PHA-L-Ala-L-Ala-L-Pro-L-Ala-L-Leu-Daunorubicin,
(3) PHA-L-Ala-L-Ala-L-Pro-L-Ala-Adriamycin,
(4) PHA-L-Ala-L-Ala-L-Pro-L-Ala-L-Leu-Adriamycin,
(5) PHA-L-Ala-L-Ala-L-Pro-L-Val-Daunorubicin,
(6) PHA-L-Ala-L-Ala-L-Pro-L-Val-L-Leu-Daunorubicin,
(7) PHA-L-Ala-L-Ala-L-Pro-L-Val-Adriamycin,
(8) PHA-L-Ala-L-Ala-L-Pro-L-Val-L-Leu-Adriamycin,
(9) PHA-L-Phe-L-Val-L-Arg-Daunorubicin,
(10) PHA-L-Phe-L-Val-L-Arg-L-Leu-Daunorubicin,
(11) PHA-L-Phe-L-Val-L-Arg-Adriamycin,
(12) PHA-L-Phe-L-Val-L-Arg-L-Leu-Adriamycin,
(13) PHA-L-Phe-L-Ala-L-Lys-Daunorubicin,
(14) PHA-L-Phe-L-Ala-L-Lys-L-Leu-Daunorubicin,
(15) PHA-L-Phe-L-Ala-L-Lys-Adriamycin,
(16) PHA-L-Phe-L-Ala-L-Lys-L-Leu-Adriamycin,
(17) PHA-Gly-Gly-L-Arg-Daunorubicin,
(18) PHA-Gly-Gly-L-Arg-L-Leu-Daunorubicin,
(19) PHA-Gly-Gly-L-Arg-Adriamycin,
(20) PHA-Gly-Gly-L-Arg-L-Leu-Adriamycin,
(21) PHA-L-Pro-L-Phe-L-Arg-Daunorubicin,
(22) PHA-L-Pro-L-Phe-L-Arg-L-Leu-Daunorubicin,
(23) PHA-L-Pro-L-Phe-L-Arg-Adriamycin,
(24) PHA-L-Pro-L-Phe-L-Arg-L-Leu-Adriamycin,
(25) PHA-L-Ile-L-Phe-L-Lys-Adriamycin,
(26) PHA-L-Ile-L-Phe-L-Lys-Daunorubicin,
(27) PHA-Gly-L-Pro-L-Lys-Adriamycin
(28) PHA-Gly-L-Pro-L-Lys-Daunorubicin,
(29) PHA-L-Val-Leu-Gly-L-Arg-Primaquine and
(30) PHA-L-Val-L-Leu-Gly-L-Arg-Chloroquine,
wherein PHA represents R$_1$—(CHOH)$_m$—CO— wherein R$_1$ represents H or CH$_3$, and m is a whole number ranging from 2 to 7.

4. The water-soluble acylated derivative of claim 3 wherein PHA is selected from the group consisting of erythronoyl, threonoyl, ribonoyl, arabinoyl, xylonoyl, lyxonoyl, gluconoyl, galactonoyl, mannonoyl, glycoheptonoyl and glycooctonoyl.

* * * * *